United States Patent [19]

Fauza

[11] Patent Number: 4,791,920
[45] Date of Patent: Dec. 20, 1988

[54] TRACHEOSTOMY CANNULA

[76] Inventor: Dario Fauza, Rua Marcondéssia No. 301, 04645 - Sao Paulo SP, Brazil

[21] Appl. No.: 82,714
[22] PCT Filed: Aug. 21, 1986
[86] PCT No.: PCT/BR86/00016
   § 371 Date: May 8, 1987
   § 102(e) Date: May 8, 1987
[87] PCT Pub. No.: WO87/01293
   PCT Pub. Date: Mar. 12, 1987

[30] Foreign Application Priority Data

Sep. 9, 1985 [BR] Brazil ................................. 8504438

[51] Int. Cl.⁴ .............................................. A61M 16/00
[52] U.S. Cl. ............................. 128/207.15; 128/207.14
[58] Field of Search ...................... 128/207.14, 207.15, 128/200.26, 342, 207.16, 207.17

[56] References Cited

U.S. PATENT DOCUMENTS

| | | | |
|---|---|---|---|
| 3,330,271 | 7/1967 | Hozer | 128/207.14 |
| 3,516,407 | 6/1970 | Ruggero | 128/325 |
| 3,543,751 | 12/1970 | Sheffer | 128/207.15 |
| 3,889,688 | 6/1975 | Eamkaow | 128/207.15 |
| 4,141,364 | 2/1979 | Schultze | 604/96 |
| 4,278,081 | 7/1981 | Jones | 128/207.15 |
| 4,280,492 | 7/1981 | Latham | 128/207.15 |
| 4,351,330 | 9/1982 | Scarberry | 128/207.15 |
| 4,449,523 | 5/1984 | Szachowicz et al. | 128/200.26 |
| 4,459,984 | 7/1984 | Liegner | 128/207.15 |
| 4,509,514 | 4/1985 | Brain | 128/207.15 |
| 4,538,606 | 9/1985 | Whited | 128/207.15 |

Primary Examiner—Lee S. Cohen
Assistant Examiner—Timothy G. Philips
Attorney, Agent, or Firm—Cushman, Darby & Cushman

[57] ABSTRACT

The present invention relates to a tracheostomy cannula with a small balloon or cuff (2) positioned posteriorly (or cranially) to the tube (1) which is consequently shorter. This tube (1) has a collar (5) that encircles the tube on its proximal portion and prevents air leakage through the stoma. The "cuff" (2) also may communicate with the environmental air by means of conduits (6) that may be flexible. Since the component structures of a cannula so formed progress only a small distance caudally into the trachea, some complications, if not completely avoided, are better guarded against. Thus, there is when using the present invention less stimulus to a coughing reflex. Moreover, its cleaning and that of the trachea are simpler, and a tracheo-innominate fistula will rarely occur.

8 Claims, 2 Drawing Sheets

TRACHEOSTOMY CANNULA

BACKGROUND OF THE INVENTION

1. Field of the Invention

The present invention relates to a tracheostomy cannula with the format and distribution of its components designed so as to prevent the so-called tracheo-innominate fistula and the smallest stimulus to the coupling reflex, and to allow the cannula to be easily cleaned.

2. Description of the Related Art

The immense majority of cannulas for tracheostomy follow a basic concept that, in itself, is the model most used today. The cannula consists of a curved tube which acts as a passage for air between the patient's trachea and the environment or an artificial respirator. Since it is often necessary to use positive inspiratory pressure by means of the above-mentioned respirators, this tube is enveloped at its caudal end by a small balloon inflatable with air or liquid, which, by adhering completely to the internal lining of the trachea by means of a cross-section of the trachea, prevents the air insufflated by the respirator from escaping into the environment and/or into the larynx and pharynx, so that air may be conducted to the caudal section of the trachea, the bronchi and pulmonary alveoli. Yet another function of this small balloon or "cuff" is to support the tube itself inside the trachea. The dimensions of the cannula vary a great deal, especially when considering pediatric models. However, for adults the limits are quite close, and the distance from the cranial edge to its distal (or caudal) extremity in an orthogonal projection parallel to the axis of the trachea is on the order of 4 to 5.5 cm. in usual models. This distance is represented by distance "x" in FIG. 1 of the invention, which will be described later.

For a better understanding of the development of the present invention, it should be noted that many complications of a tracheostomy depend on irritations caused by the tube itself and/or by the small balloon. Thus, the longer the cannula tube, the greater the stimulus to coughing and the harder it is to clean both the cannula and the trachea. However, the greatest aggravating factor of such cannulas are the lesions to the trachea walls and/or to structures contiguous to the trachea which are produced by the possible compression exerted on these tissues by the tube, mainly in its caudal extremity and/or by the small balloon, especially if the pressure in the trachea's interior is very high. Such lesions range from a simple ischaemia to real perforations, with resulting secondary complications that are essentially obstructive, infectious and/or hemorrhagic. Among the latter can be noted the so-called tracheo-innominate fistual - an abnormal passage between the trachea and the innominate artery through such perforations. This fearful intercurrent process may cause severe hemorrhages which, when they do occur, lead to a case fatality rate of over 92%. Its occurrence is intimately related to the dimensions of the cannula: the longer it is, the greater the risk to the patient. This risk is already uncommonly high since the distance from the upper limit of the second cartilagineous trachial ring-cranial limit of the great majority of tracheostomies, up to the upper crossing point of the trachea with the innominate artery is, on the average for adults, about 3.3 cm, whereas the same distance measured on the cannula to its caudal extremity is approximately between 4 and 5.5 cm, as mentioned above.

Another "inconvenience", not properly a complication, in the use of these tracheostomy cannulas of the prior art is the need for a tape to be fitted around the neck of the patient and tied to the proximal extremity of the cannula in order to hold and fix it in place. However, there is a known model on the North American market which, among other small improvements, does away with the use of tapes around the neck and lends itself to the prevention of this tracheo-innominate fistula. It consists of a simple tube placed between the skin of the neck and the anterior wall of the trachea, and it is fixed there by its proximal and distal edges. Since it does not progress caudally along the interior of the trachea, if it does not do away with, it greatly reduces the risk of the onset of this complication. This cannula only hides the tracheal stoma without, however, allowing the use of positive inspiratory pressure through artificial respirators, which renders its use impossible in various patients to be tracheostomized. Besides, it is difficult to remove them from the tracheal stoma and these may, although on a smaller scale, lead to infectious, obstructive or hemorrhagic complications.

In short, whatever the model to be considered, there is still the risk of irritation on the part of the components of the cannula of the prior art, and the consequences tend to be more severe the more caudally these components progress through the interior of the trachea.

SUMMARY OF THE INVENTION

With the objective of generally decreasing the irritative potential of tracheostomy cannulas, but particularly concerning the lesser stimulus to the coughing reflex, ease in cleaning both the cannula and the trachea, and preventing a tracheo-innominate fistula, the cannula of the present invention was developed to include a small balloon or "cuff" positioned in the region posterior to the curved tube, which, by this positioning, allows a reduction in its length.

BRIEF DESCRIPTION OF THE DRAWING

The tracheostomy cannula of the present invention may be better understood by the description of the diagrams enclosed, which represent.

DETAILED DESCRIPTION OF THE PREFERRED EMBODIMENT

Figure 1:
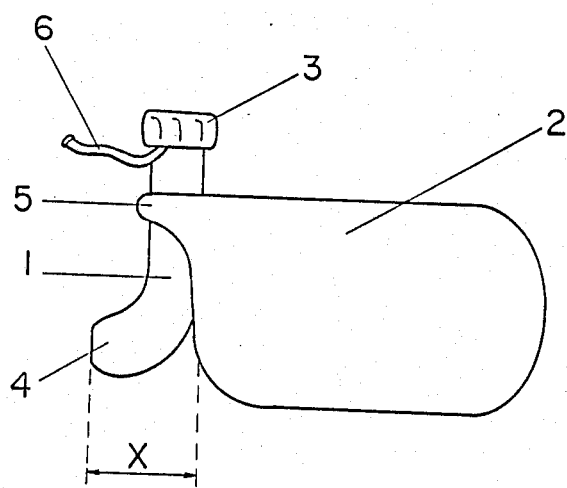
FIG. 1—Side view in elevation of the tracheostomy cannula of the present invention.
Figure 2:
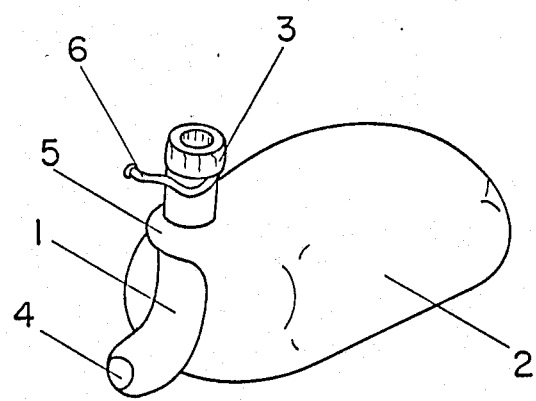
FIG. 2—View in perspective of this same cannula of FIG. 1.

As can be seen from FIGS. 1 and 2, the tracheostomy cannula of the present invention consists of a curved tube (1) with a circular contour in cross-section, but which is quite short, with the distance "x" being equal to about 1 cm which, besides decreasing the coughing reflex and facilitating the cleaning both of the cannula and of the trachea, drastically reduces or possibly eliminates the risk of occurrence of a tracheo-innominate fistula since the caudal extremity of the tube generally will not reach the region of the crossing of the trachea with the innominate artery, also known as the brachio-cephalic trunk. Its extremity, known as proximal (3), or, in order words, that portion which is exposed to the environment on introduction of the cannula into the trachea, is equally circular in contour to the cross-section of the tube (1), but is has a radius that is slightly larger than that of the tube and adaptable to artificial tracheas. The distal or caudal extremity (4), which is inside the trachea, also has a circular contour accompanying the tube; however, its radius is slightly smaller than the radius of the tube, which renders its edge flatter and thereby lessens irritation to the trachea wall since, as is known, it is this edge of the distal extremity that is primarily responsible for lesions.

The small balloon or "cuff" (2) is placed posteriorly to the tube, with the anterior or caudal portion closely adhering to it. Such positioning of the "cuff" should do away with the risk of the onset of a tracheo-innominate fistula which is generally a result of a possible irritation to the wall of the trachea, for the "cuff" will be far from the crossing of the trachea with the innominate artery. This "cuff" (2) also has an anterior extension which involves all of the proximal third of the tube (1) to form a "collar" (5) which, together with the configuration of the proximal extremity of the tube (1), will help to fix the cannula to the site, thereby dispensing with the uncomfortable use of tapes around the neck and preventing the possible escape of air insufflated under positive pressure into the environment. Since the "cuff" (2) can progress as far as the larynx on a level with the vocal cords, it will have great restraining capacity. Moreover, because it will not have a tube crossing it, as in the unusual models, with the resultant low pressure in its interior, the cannula of the present invention considerably reduces the capacity for irritation to the endotracheal lining. In addition, the contour of this "cuff" (2) in cross-section to the craniocaudal axis should be similar to the endotracheal lining of the majority of persons on this same plane, or, in other words, is elliptical, with a greater latero-lateral axis.

Control of pressure, and also the insufflation and deflation of the "cuff" (2), takes place by means of conduits (6) which may be flexible, and which connect the interior of the "cuff" (2) with the environment. The conduits (6) are fitted with caps, which may have a valve, as in the case of other models of the prior art.

The material making up the cannula components should be as inert as possible - that is, they should promote the least possible reaction, or none at all, between the body and the instrument. For instance, polytetrafluorethylene, polyvinyl and many others may be used.

The tracheostomy cannula of the invention may, starting from the basic concept described above, undergo some changes such as in its dimensions, which vary according to the patient's anatomical characteristics. For example, the curved tube may have two "central cavities", or in other words, an internal removable lining for cases of acute obstruction or for facilitating cleaning. Also, the caudal extremity (4) may be designed so as not to be flat, should such a feature increase the resistance to the air flow in very small cannulas. However, this fact is almost impossible to occur. In addition, the proximal extremity may be removable, and in such a case, it will be coupled to the tube, for instance, by means of threading which may lead it to the skin of the patient's neck, should this contribute to fixing the cannula in place. The tube also may have contours other than a circular cross-section, and the anterior extension or "collar" (5) may be of varied configurations, ranging from one analogous to that presented in FIGS. 1 and 2 to that in which it lines all of the intratracheal portion of the tube as far as its distal extremities, which may contribute to increasing the restraining capacity of the "cuff" (2) with a resulting low pressure in its interior and/or for better holding of the cannula. This same "collar" (5) also may be totally or partly adherent to the tube. Its mobility, should it not be adhered, should facilitate sealing of the tracheal stoma, particularly when the dimensions of the trachea, principally the anteroposterior diameter, are extremely variable. The "collar" (5) also may communicate with the main compartment of the "cuff" (2), just as it may be of inflatable material. Pressure within the "cuff" (2) may be controlled by valves, as is already the case in other models, and the "cuff" (2) may be fitted with two separate compartments so that one compartment may be insufflated while the second is not, and vice-versa. This may occur alternately, which may decrease irritation to the tracheal wall without loss of function, as occurs in the case of periodic deflation of common "cuffs". The "cuff" (2) may (preferably) have all of its anterior portion adhering to the tube so as to always retain some adhesion. Also, the contour of the "cuff" may assume forms other than elliptical, according to the anatomical characteristics of the patient. In some rare cases it should be noted that it may be necessary to wear tapes around the neck, which are attached to the proximal portion of the cannula. Finally, the material making up the cannula may be of any kind, with preference being given, however, and logically so, to the more "inert" types.

The functions of the tracheostomy cannula of this invention are thus the same as the "traditional" one. Its insertion into the patient is effected by means of the classic tracheostomy techniques, and it is introduced into the trachea with the "cuff" totally deflated. Then, once it is in place, it is insufflated. As in existing models, insufflation and deflation, and also the control of pressure inside the "cuff", is done by means of small sealable conduits that connect the interior of the small balloon to the environment.

I claim:

1. A tracheostomy device for introduction into the trachea of a patient to form an artificial airway through the patient's throat, comprising:

a hollow tube having proximal and distal end portions and a bend intermediate of said end portions so as to form first and second portions of said tube respectively including said proximal and distal end portions of said tube, said proximal end portion having a radius slightly larger than that of said first portion of said tube and said distal end portion being arranged for insertion through a tracheal stoma and into a tracheal lumen of the patient's throat such that said second portion of said tube extends in a first direction within the tracheal lumen when said first portion extends through the tracheal stoma;

an inflatable cuff;

means for adhering said inflatable cuff to said tube and for directing said cuff when inflated such that said cuff extends within the tracheal lumen of the patient's throat only in a second direction substantially opposite to said first direction; and means for inflating and deflating said cuff.

2. A tracheostomy device as in claim 1, wherein said cuff comprises a small balloon.

3. A tracheostomy device as in claim 1, wherein said inflating and deflating means comprises at least one flexible conduit.

4. A tracheostomy device as in claim 1, wherein said adhering and directing means comprises a collar which is movable along said tube.

5. A tracheostomy device as in claim 1, wherein said adhering and directing means comprises a collar which is inflatable.

6. A tracheostomy device as in claim 5, wherein said collar communicates with said cuff.

7. A tracheostomy device as in claim 1, wherein said cuff is of such a size when expanded so as to expand within the limits of the tracheal lumen as far as the patient's larynx in order to restrain said tube within the patient's trachea when said tracheostomy device is inserted into the trachea of the patient.

8. A tracheostomy device as in claim 7, wherein said adhering and directing means comprises a collar which is disposed on said first portion of said tube so as to prevent air leakage through the tracheal stoma when said tracheostomy device is inserted into the trachea of the patient.

* * * * *

UNITED STATES PATENT AND TRADEMARK OFFICE
CERTIFICATE OF CORRECTION

PATENT NO.  : 4,791,920

DATED       : December 20, 1988

INVENTOR(S) : FAUZA

It is certified that error appears in the above-identified patent and that said Letters Patent is hereby corrected as shown below:

Col. 1, line  9, change "coupling" to -- coughing --;

line 56, change "fistual" to -- fistula --;

line 64, change "trachial" to -- tracheal --.

Col. 2, line 65, change "order" to -- other --;

line 68, change "is" to --  it -- (first occurrence).

Col. 3, line 27, change "unusual" to -- usual --.

Signed and Sealed this

Seventeenth Day of October, 1989

Attest:

DONALD J. QUIGG

Attesting Officer      Commissioner of Patents and Trademarks